(12) United States Patent
Novik

(10) Patent No.: US 10,390,696 B2
(45) Date of Patent: Aug. 27, 2019

(54) DYNAMIC COMPUTER IMAGES FOR IMPROVING VISUAL PERCEPTION

(71) Applicant: EYEKON E.R.D. LTD., Ramat Gan (IL)

(72) Inventor: Shai Novik, Ramat Hasharon (IL)

(73) Assignee: EYEKON E.R.D. LTD., Ramat Gan (IL)

( * ) Notice: Subject to any disclaimer, the term of this patent is extended or adjusted under 35 U.S.C. 154(b) by 11 days.

(21) Appl. No.: 15/527,026

(22) PCT Filed: Nov. 26, 2015

(86) PCT No.: PCT/IL2015/051148
§ 371 (c)(1),
(2) Date: May 16, 2017

(87) PCT Pub. No.: WO2016/084083
PCT Pub. Date: Jun. 2, 2016

(65) Prior Publication Data
US 2017/0347874 A1    Dec. 7, 2017

Related U.S. Application Data

(60) Provisional application No. 62/084,592, filed on Nov. 26, 2014, provisional application No. 62/237,604, filed on Oct. 6, 2015.

(51) Int. Cl.
*A61B 3/14* (2006.01)
*A61B 3/00* (2006.01)
(Continued)

(52) U.S. Cl.
CPC .............. *A61B 3/032* (2013.01); *G06F 3/015* (2013.01); *G06F 3/016* (2013.01); *G10L 17/005* (2013.01)

(58) Field of Classification Search
CPC ..... A61B 5/6803; A61B 3/0025; A61B 3/024; A61B 3/032; A61B 3/113; A61B 3/14;
(Continued)

(56) References Cited

U.S. PATENT DOCUMENTS 6,045,227 A     4/2000  Steward et al.
2005/0243277 A1  11/2005  Nashner
(Continued)

FOREIGN PATENT DOCUMENTS

WO    WO 2001/047463 A1    7/2001

OTHER PUBLICATIONS

Achtman et al. "Video games as a tool to train visual skills" Restorative neurology and neuroscience. Jan. 1, 2008;26(4, 5):435-46.

(Continued)

*Primary Examiner* — Brandi N Thomas
(74) *Attorney, Agent, or Firm* — Mark Cohen; Pearl Cohen Zedek Latzer Baratz LLP

(57) ABSTRACT

Methods for presenting dynamic images to a user, configured to evaluate and/or improve the user's foveal and/or peripheral visual acuity. Dynamic computer games are popular, but the moving images of prior art dynamic computer games are not suitable for improving visual acuity. To overcome this restriction, embodiments of the present invention analyze user's responses to the moving images to determine a change in the user's visual acuity, and responsively adjust parameters of the moving images, such as speed, direction of motion, orientation, crowding, contrast, and spatial frequency, in order to improve the user's visual acuity.

20 Claims, 10 Drawing Sheets

(51) Int. Cl.
*A61B 3/032* (2006.01)
*G06F 3/01* (2006.01)
*G10L 17/00* (2013.01)

(58) Field of Classification Search
CPC ............ A61B 2562/0219; A61B 3/028; A61B 3/1015; A61B 3/112; A61B 3/13; A61B 5/4064; A61B 2562/0204; A61B 2562/0238; A61B 2562/0247; A61B 2562/04; A61B 3/0008; A61B 3/003
USPC ........ 351/200, 205, 206, 209–212, 221–223, 351/243–246
See application file for complete search history.

(56) References Cited

U.S. PATENT DOCUMENTS

| | | | | |
|---|---|---|---|---|
| 2007/0076168 | A1* | 4/2007 | Ellenbogen | A61B 3/022 351/200 |
| 2011/0116047 | A1* | 5/2011 | Polat | A61B 3/0033 351/239 |
| 2012/0050685 | A1* | 3/2012 | Bartlett | A61B 3/0033 351/223 |
| 2012/0327369 | A1 | 12/2012 | Hytowitz | |
| 2014/0168606 | A1 | 6/2014 | Berry et al. | |

OTHER PUBLICATIONS

Appelbaum et al. "Action video game playing is associated with improved visual sensitivity, but not alterations in visual sensory memory" Attention, Perception, & Psychophysics. Aug. 1, 2013;75(6):1161-7.
Baron et al. "Visual acuity as a function of exposure duration" JOSA. Feb. 1, 1973;63(2):212-9.
Bolz et al. "The role of horizontal connections in generating long receptive fields in the cat visual cortex" European Journal of Neuroscience, May 1989;1(3):263-8.
Bosking et al. "Orientation selectivity and the arrangement of horizontal connections in tree shrew striate cortex" Journal of neuroscience. Mar. 15, 1997;17(6):2112-27.
Buckley et al. "Action video game players and deaf observers have larger Goldmann visual fields" Vision research. Mar. 5, 2010;50(5):548-56.
Das et al. "Long-range horizontal connections and their role in cortical reorganization revealed by optical recording of cat primary visual cortex" Nature, Jun. 1995;375(6534):780; Abstract.
Dye et al. "Increasing speed of processing with action video games" Current directions in psychological science. Dec. 2009;18(6):321-6.
Flom et al. "Contour interaction and visual resolution: Contralateral effects" Science. Nov. 15, 1963;142(3594):979-80.
Flom et al. "Visual resolution and contour interaction" JOSA. Sep. 1, 1963;53(9);1026-32.
Green et al. "Action video game modifies visual selective attention" Nature. May 2003;423(6939):534.
Green et al. "Effect of action video games on the spatial distribution of visuospatial attention" Journal of experimental psychology: Human perception and performance. Dec. 2006;32(6):1465.
Green et al. "Enumeration versus multiple object tracking: The case of action video game players" Cognition. Aug. 1, 2006;101(1):217-45.
Green et al."Action-video-game experience alters the spatial resolution of vision" Psychological science. Jan. 2007;18(1):88-94.
Hubel et al. "Receptive fields, binocular interaction and functional architecture in the cat's visual cortex" The Journal of physiology. Jan. 1, 1962;160(1):106-54.
Hubel et al. "Receptive fields and functional architecture of monkey striate cortex" The Journal of physiology. Mar. 1, 1968;195(1):215-43.
International Search Report for PCT Application No. PCT/IL2015/051148 dated Feb. 25, 2016.
Kapadia et al. "Improvement in visual sensitivity by changes in local context: parallel studies in human observers and in V1 of alert monkeys" Neuron. Oct. 1, 1995;15(4):843-56.
Lev et al. "Uncovering foveal crowding?" Scientific reports. Feb. 12, 2014;4:4067.
Levi DM. "Crowding—An essential bottleneck for object recognition: A mini-review" Vision research. Feb. 1, 2008;48(5):635-54.
Li et al. "Enhancing the contrast sensitivity function through action video game training" Nature neuroscience. May 2009;12(5):549.
Li et al. "Reducing backward masking through action game training" Journal of Vision. Dec. 1, 2010;10(14):33-.
Li et al. "Video-game play induces plasticity in the visual system of adults with amblyopia" PLoS biology. Aug. 30, 2011;9(8):e1001135.
Paradis et al. "Speeding up the brain: when spatial facilitation translates into latency shortening" Frontiers in human neuroscience. Dec. 19, 2012;6:330.
Polat U. "Functional architecture of long-range perceptual interactions" Spatial vision. Jan. 1, 1999;12(2):143-62.
Polat U. "Making perceptual learning practical to improve visual functions" Vision research. Oct. 29, 2009;49(21):2566-73.
Polat et al. "Improving vision in adult amblyopia by perceptual learning" Proceedings of the National Academy of Sciences. Apr. 27, 2004;101(17):6692-7.
Polat et al. "Collinear stimuli regulate visual responses depending on cell's contrast threshold" Nature. Feb. 1998;391(6667):580.
Polat et al. "The architecture of perceptual spatial interactions" Vision research. Jan. 1, 1994;34(1):73-8.
Polat et al. "Temporal asymmetry of collinear lateral interactions" Vision research. Mar. 1, 2006;46(6-7):953-60.
Polat et al. "Spatio-temporal low-level neural networks account for visual masking" Advances in Cognitive Psychology. 2007;3(1-2):153.
Polat et al. "What pattern the eye sees best" Vision research. Mar. 14, 1999;39(5):887-95.
Sagi D. "Perceptual learning in vision research" Vision research. Jul. 1, 2011;51(13):1552-66.
Schwarz et al. "Functional specificity of a long-range horizontal connection in cat visual cortex: a cross-correlation study" Journal of Neuroscience. Oct. 1, 1991;11(10):2995-3007.
Supplementary European Search Report for European Application No. 15864113.4 dated Jul. 4, 2018.

* cited by examiner

Static Visual Acuity test

DYNAMIC COMPUTER IMAGES FOR IMPROVING VISUAL PERCEPTION

BACKGROUND

Visual perception concerns the ability of people to detect and recognize visual objects, and is related to visual acuity (VA), which is the most commonly-used measure of human visual function. A person with standard (normal) VA can recognize a letter or symbol that subtends an angle of 5 arc minutes. Clinically, a level of VA specified as 6/6 (meters) or 20/20 (feet) is considered good "normal" vision. Other factors associated with visual perception include the time required for visual processing, and the ability to discriminate visual regions having different contrast levels. Therefore, measures of visual acuity herein include a measure of the ability to see a given object size at a given duration of exposure and/or at a given contrast level.

Static computer games (which involve no movement of images, and have only static images with changes to contrast and other parameters) have shown a potential to significantly improve foveal and peripheral visual acuity. However, dynamic computer games (based on movement of images) have currently shown no noticeable effect on foveal or peripheral visual acuity. To the contrary, it is believed that the movement of images on the screen restricts the ability to improve visual acuity.

Prior art studies, show no benefit of dynamic computer game training on foveal or peripheral visual acuity, thereby in practice ruling out the use of dynamic computer games for improving vision, in sharp distinction to the significant improvement on visual acuity afforded by the playing of static computer games. As noted, the prior art teaches that a dynamic computer game, by forcing players to follow the movement of dynamic visual objects on the screen, does not contribute to improvements in foveal or peripheral visual acuity.

SUMMARY

Various embodiments of the present invention provide dynamic computer games based on movement of images that effect a significant improvement in foveal and/or peripheral visual acuity.

According to certain embodiments of the invention, improvement of players' visual acuity through processing of neurons is achieved by stimulating visual neurons in the brain to improve their dynamic response, through the use of moving visual elements on the screen in specific directions and at specific speeds. Physical parameters, such as speed, are modified to increase the difficulty level. The starting difficulty level is adjusted to each user's base difficulty level, and is increased according to the pace of improvement.

It is known that neural response R increases with increasing presentation time t and the contrast of the stimulus E (energy), and thus, the response of a neuron over a linear response region can be approximated by $$R=tE. \qquad \text{[Equation 1]}$$

R increases with increasing E and/or t until reaching saturation level, known as critical duration. Thus, in order to evoke optimal neural response, certain embodiments of the invention use optimal values of t and E. According to these embodiments, even when the physical parameters (contrast, orientation, and spatial frequency) are optimal, but t is too short, the total activation is not efficient in increasing R to its optimal level.

On the other hand, R, or contrast sensitivity (CS), is reduced for moving targets compared to static targets. In an embodiment of the present invention, this is attributed to target movement across a neuron's classical receptive field (CRF) such that the time the target spends in the neuron's CRF is less than the time t needed for optimal neural response. It is known that visual sensitivity and visual acuity increase with longer presentation time, until they reach critical duration. Therefore, when the target is moving, it evokes response from a neuron only for the limited time that it appears within the neuron's visual field (CRF). When the target moves at a certain speed v, the time t that it is presented on the CRF decreases with increasing speed. If d is the length of the target's trajectory across the neuron's CRF, then $$t=d/v. \qquad \text{[Equation 2]}$$

If $d_R$ is taken as a representative (constant) value of the target trajectory length across neural CRF's, then a representative time $t_R$ is given by $$t_R=d_R/v. \qquad \text{[Equation 3]}$$

That is, $t_R$ is inversely proportional to v, with $d_R$ as the coefficient of proportionality.

Therefore, in various embodiments of the present invention, the speed of a target's movement is adjusted to optimally activate neural response, increasing the efficiency of neural response by improving the integration time t of the target information.

It is known that the users tend to perceive a target moving at a given speed as moving faster when the motion is in the collinear direction. When the target is moving, it activates different neurons along the trajectory. The brain integrates the discrete segments of local motion signals from many neurons into a perceived global, smooth continuous trajectory of motion. In various embodiments of the invention, therefore, efficiency of neural connectivity between adjacent neurons along a target trajectory is very important for acquiring and properly interpreting moving target content. Improvement of this processing improves the vision of non-moving stimuli as well.

Unlike dynamic computer games that may improve visual performance indirectly but have no effect on visual acuity, embodiments of the present invention are configured specifically for target acquisition and for improving visual acuity by optimizing dynamic parameters. In various embodiments, different neurons are tuned to different orientations and different spatial frequencies. Therefore, certain embodiments of the invention are configured to systematically train users with combinations of different target speed at different orientations and different spatial frequencies for improving the speed of visual processing. In addition, because visual perception and acuity deteriorate with increasing target speed, related embodiments specifically determine the relevant speed and size parameters to optimally stimulate the visual neurons. In these embodiments, gaming algorithms are structured and tailored to each user according to the pace of the improvement after reaching a desired performance level. The target speed is adjusted to optimally stimulate the spatial frequency of the underlying CRF.

Thus, according to various embodiments of the invention, in order to improve visual skills, a dynamic computer game should be fast-paced and unpredictable. The fast pace demands frequent user interaction and provides multiple learning opportunities, where each action is met with some form of behavioral reinforcement. The lack of predictability (events of unknown time of arrival and location) enforces distributed attention and results in sufficiently-frequent user errors to signal when behavioral adjustments are needed, promoting a high level of active engagement and learning. In certain related embodiments, correct responses are met with high reward. Thus, in some embodiments, a game's difficulty is adaptable, in order for each player to be engaged at a level that is challenging yet not overwhelming Dynamic computer games according to embodiments of the present invention serve to improve the foveal and peripheral visual acuity of users of the games, by overcoming prior art restrictions in which dynamic computer games featuring moving images are not conducive to such improvement.

BRIEF DESCRIPTION OF THE DRAWINGS

The subject matter disclosed herein may best be understood by reference to the following detailed description when read with the accompanying drawings in which.

Figure 1:
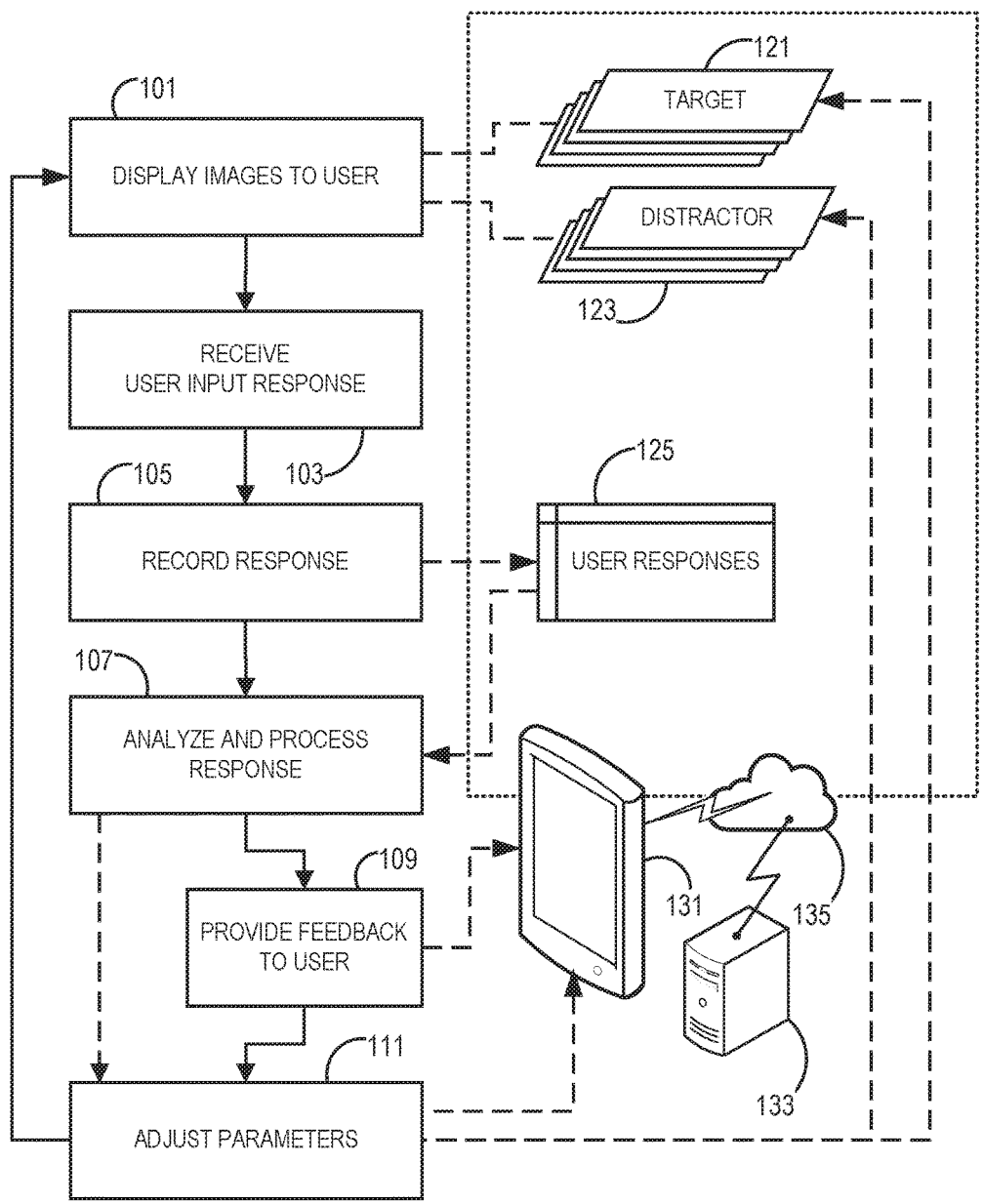
FIG. 1 is a flowchart of a method for presenting dynamic computer images to evaluate and/or improve user visual acuity, according to an embodiment of the present invention.

For simplicity and clarity of illustration, elements shown are not necessarily drawn to scale, and the dimensions of some elements may be exaggerated relative to other elements. In addition, reference numerals may be repeated to indicate corresponding or analogous elements.

DETAILED DESCRIPTION

The following description is provided, alongside all chapters of the present invention, so as to enable any person skilled in the art to make use of the invention and sets forth the best modes contemplated by the inventor of carrying out this invention. Various modifications, however, are adapted to remain apparent to those skilled in the art, since the generic principles of the present invention have been defined specifically to provide a method, a device and a computer readable medium (CRM) for presenting dynamic-images to evaluate and/or improve a user's visual acuity.

Games typically involve play, and are often structured around formal goals and rules of interaction. In the context of some embodiments of the present invention, the term "user", used herein, denotes a player of a computer game. The term "computer game" herein denotes any user-interactive computer- or microprocessor-controlled game having a visual display, including games commonly referred to as "video games". Computers can create virtual spaces for a wide variety of game types. Some computer games simulate conventional game objects like cards or dice, while others can simulate environments grounded in reality and/or in fantasy, with their own rules and goals.

The term "computer game-playing device", as used herein, denotes according to some embodiments any device capable of displaying a computer game and interactively operating the game with a player. For brevity in the descriptions, the terms "device" and "user device" are also used herein to denote a "computer game-playing device". Computer game-playing devices include, but are not limited to: computers of all kinds, game consoles, television sets, arcade game systems, cellular telephones, tablet computers, workstations, terminals, and the like. A game for a computer game-playing device is typically supplied as a product containing machine-readable executable code, which, when executed, causes the device to present the game to a user.

The term "present a game", according to some embodiments, denotes displaying the game to the user on a display screen, along with associate audio effects (if any), to receive user input related to playing the game, and to process user input for playing the game.

A computer game-playing device typically has one or more user-inputs, including, but not limited to: a button/joystick combination (on arcade games); a keyboard, mouse and/or trackball (on computer games); a touchscreen; an accelerometer or combinations of accelerometers for detecting changes in orientation or position of a personal user device (such as a smartphone or tablet computer); or a controller or a motion sensitive tool (on console games). More esoteric devices such as paddle controllers and cameras have also been used for input. Most computer games are intended to be entertaining for the user.

Embodiments of the present invention rely on dynamic images. The term "dynamic", in the context of images, as used herein, denotes an image that perceptibly changes in orientation and/or position as time progresses (e.g., a moving or non-stationary image). In the case of orientation, a change of orientation is understood to include a rotation of a three-dimensional object (virtual or real) which is projected onto a two-dimensional surface, a non-limiting example of which is a two-dimensional image of a spinning globe. A dynamic image need not be constantly changing in orientation and/or position: an image may remain perceptibly unchanging for a time and may still be considered a "dynamic" image, provided that the image is capable of being perceptibly changed in orientation and/or position, and be readily perceived as moving by an observer.

In distinction, the term "static", in the context of images, as used herein, denotes an image that does not perceptibly change in size, shape, orientation, and/or position as time progresses. A static image, however, may change perceptibly in brightness, contrast, and/or color as time progresses. In particular, a static image may be made visible and/or non-visible as time progresses.

The terms "dynamic" and "static", as used herein, are mutually-exclusive, in that dynamic images are non-static, and static images are non-dynamic As set forth above, embodiments of the present invention rely on dynamic images. Accordingly, unless explicitly noted to the contrary, all references to images and visual objects herein are references to dynamic images. For brevity in the descriptions, the "dynamic" qualifier is generally omitted. Thus, in a non-limiting example, a reference herein to a "target image" is understood to be a reference to a "dynamic target image".

The term "target", as used herein, denotes an image on a computer game-playing device display that a user is to visually acquire, and, in some cases to identify. In this context, a target image need not necessarily be an object to attack or strike.

The term "distractor", as used herein, denotes an image on a computer game-playing display that a user is to visually bypass. In some cases, distractor images are intentionally included on a computer game-playing device display to visually confuse the user, and to make it harder for the user to visually discriminate, acquire, and/or identify a particular target.

The terms "Backward masking", as used herein, refers to presenting one visual stimulus (a "mask" or "masking stimulus") immediately after another brief "target" visual stimulus.

The terms "Lateral masking", as used herein, refers to presenting identical or similar entities in close proximity.

The term "time-step", as used herein, refers to a particular time period at which a series of several actions or steps is performed. A non-limiting example may include: displaying images, receiving user's response, analyzing the response, and adjusting the images for the following series of actions, at the next or at least one of the following time-step/s. Each of series, at each time-step, may or may not include all of the defined actions or steps. The reference "n" is used herein to indicate the number of the time-step (n=1, 2 ... k−1, k, k+1, ... K).

The term "visual acuity", as used herein, refers to the clarity of vision. Visual acuity is dependent on optical and neural factors, i.e., (i) the sharpness of the retinal focus within the eye, (ii) the health and functioning of the retina, and (iii) the sensitivity of the interpretative faculty of the brain. Measures of evaluation of the visual acuity, according to some embodiments of the present invention, refer to visual abilities related to: ability to see a given object size at a given duration of exposure and/or at a given contrast level light sensitivity, contrast sensitivity, visual crowding, backward masking, depth perception. Factors associated with visual perception include the time required for visual processing, and the ability to discriminate visual regions having different contrast levels and various visual crowding conditions. Further, measures of evaluation of the visual acuity, according to some embodiments of the present invention, include a measure of the ability to see a given object size at a given duration of exposure and/or at a given contrast level.

Utilizing Computer Games to Improve Visual Functions

It is known that an individual can improve performance in a given task by training on that task. The improvement is typically limited to the trained task and shows little to no generalization into different, even highly related, tasks. This specificity applies in the field of perceptual learning, which can be very specific to the trained eye, direction of motion, or even retinal location. This specificity is a major limitation in using perceptual learning for practical purposes such as visual improvement.

Using computer games to improve visual skills is an area of interest. The possibility that players of computer games gain enhanced perceptual and cognitive abilities has attracted much attention. Studies show that playing computer games results in some enhancement of visual tasks in adults with normal vision, such as light sensitivity, contrast sensitivity, visual crowding, backward masking and visual attention.

Thus, computer games according to various embodiments of the present invention the games are intended for people with "normal" (e.g., 20/20) vision as well as for people with reduced visual acuity. Even people with normal vision can experience improvement in their visual perception by playing these games, where the improvement includes, for example, an increase in visual processing speed, and thus improvements in visual perception of certain objects seen at limited time exposure.

Categories of Dynamic Computer Games

Unpredictable Event Games—This category includes first-person and third-person action games. They place heavy demands on visual attention, requiring players to constantly monitor the visual area for frequent, widely distributed, unpredictable events that require quick and accurate aiming responses. Players need to track many fast moving objects while ignoring distractors. Most significantly, unpredictable event games require motor actions that are spatially aligned with the detailed visual world of the game, typically where missing a target results in some kind of penalty for the player.

Sports or Racing Games—This category, like unpredictable event games, places heavy demands on visual attention, requiring players to constantly monitor the visual area, although experienced users can be able to anticipate typical events and conditions.

Visio-Motor Control Games—Games in this category (e.g., Tetris) typically require rapid visual target acquisition and analysis, but lack both unpredictable events and distractors.

Strategy Games—These games are typically not fast-paced. Displays can be visually complex, and although it may be necessary to keep track of multiple visual objects, strategy games typically focus on cognitive tactics and planning rather than challenges to the visual system.

Puzzle and Card Games—In games of this category, players can choose how to allocate their attention. At no point are there unexpected events or visual challenges. Responses typically have no time limits or requirements for spatially accuracy, but rather rely on problem-solving abilities often aided by memory skills.

Static Vs. Dynamic Computer Games and Effect on Visual Acuity

The difference between a static computer game and a dynamic computer game centers on the movement of visual elements of the game.

In a static game, once a static image has been presented to the player, that static image is fixed on the screen, and does not move to other locations on the screen. In a static game, the static images can change their properties during the presentation on the screen, but not move. Non-limiting examples include: a static image can be presented for a very short duration of time and then disappear; and a static image can be presented using weak contrast and then change to stronger contrast, while remaining at the same location on the screen.

In a dynamic game, once a dynamic image has been presented to the player, that dynamic image is not necessarily fixed on the screen and can move to other locations on the screen requiring the player to follow that movement, in order to reach the game's objectives.

It is known that utilizing specific static games can result in significant gains in foveal or peripheral visual acuity, and that temporal aspects of early visual processing are altered by playing static computer games. Temporal masking studies provide a measure of the time needed for visual processing. For instance, measuring the contrast threshold of a static image Gabor patch flanked in time (as opposed to space) by other static image Gabor patches is known, as well as the disruption of the visibility of a briefly presented static target when a mask is presented shortly thereafter. Training using backward masking is also known to improve visual acuity.

The popularity of dynamic computer games, however, means that people may be more attracted to dynamic games than to static games. It would therefore be highly desirable to have a means of presenting dynamic computer games with the capability of improving visual perception of a player. This goal is met by embodiments of the present invention.

Diagnosis of Medical Conditions Affecting Visual Function

Certain embodiments of the present invention provide tests for differential diagnosis of medical conditions affecting visual function. In differential diagnosis, several possible diagnoses are compared and contrasted, involving the correlation of various observations and test results followed by the recognition and differentiation of patterns.

Differences between conditions are typically based on data collected from groups of subjects, and decisions about specific condition are then made by comparing different groups according to statistical measures. Unfortunately, this does not adequately address the case where a decision needs to be made according to a single test. In this case, the true positive and false positive rates reveal the sensitivity and specificity of the test. High sensitivity and high specificity increase the probability of correct diagnosis. Typically, however, there is a significant overlap between true positive and false positive, thereby impacting the ability to make a correct decision from a single test. That is, the difference between groups often relies on statistical factors, making it difficult to decide which group a subject is in without further testing. In particular, it is known in the art that the contrast sensitivity of patients with glaucoma or retinopathy is different from the contrast sensitivity of normal-vision control groups. However, the difference is between the group averages, and the specificity is not high, especially when testing non-severe conditions, so that there is a large overlap.

Specific embodiments of the present invention provide automated diagnosis of certain vision deficiencies to overcome the above restrictions, by combining several different tests into one or more dynamic computer games. Testing according to these embodiments can accumulate additional data, and it is possible to attain high probability levels for diagnosis of conditions including, but not limited to: glaucoma, retinopathy, amblyopia, presbyopia; and disabilities such as ADHD and dyslexia. In related embodiments, differentiation is based on a function of affected spatial frequencies.

The advantages provided by embodiments of the present invention can be seen in a non-limiting example involving diagnosis of disabilities, such as attention deficit/hyperactivity disorder (ADHD), a common behavioral disorder with a genetic component. Diagnosis of ADHD is typically performed by clinicians using subjective tools and questionnaires, or by computerized continuous performance tests (CPT) with uncertain reliability as screening diagnostic tools. Using prior art methods, it is often difficult to reach objective conclusion due to high variance, false positives, and the inability to perform remote self-testing.

Therefore, according to an embodiment, disclosed herein a method for presenting dynamic-images configured to evaluate and/or improve user's visual acuity, the method comprising processor implemented steps of:
  displaying, at a given time-step ($n=k$), one or more dynamic-images to a user, via a display-device;
  receiving, at the given time-step ($n=k$), the user's response to the displayed dynamic-image/s, via an input-interface, where the lack of a response is also considered as a response;
  analyzing, one or more of the user's responses ($n \leq k$), received at the given time-step ($n=k$) and/or at former time-step/s ($n<k$), to determine a change in the user's visual acuity, where the lack of a change is also considered and analyzed; and
  adjusting, for at least one of the following time-steps ($n>k$), one or more parameters of at least one of the dynamic-images, responsively to a predetermined threshold for the change or a predetermined state of the change.

According to an embodiment, disclosed herein a device configured to display dynamic images to evaluate and/or improve a user's visual acuity, comprising:
  at least one display-device, configure to display, at a given time-step ($n=k$), one or more dynamic-images to a user;
  at least one input-device, configured to collect and interpret or take to mean, at the given time-step ($n=k$), the user's response to the displayed dynamic-image/s, where the lack of a response is also considered as a response; and
  at least one processor configured to:
    analyze, one or more of the user's responses ($n \leq k$), received at the given time-step ($n=k$) and/or at former time-step/s ($n<k$), to determine a change in the user's visual acuity, where the lack of a change is also considered and analyzed; and
    adjust, for at least one of the following time-steps ($n>k$), one or more parameters of at least one of the dynamic-images, responsively to a predetermined threshold for the change or a predetermined state of the change.

According to some embodiments, the input-device is configured to perform at least one of:
  collect tactile- and/or touch-input of the user;
  recognize voice response of the user;
  monitor and observe eye-movement of the user.

According to some embodiments, the display-device is configured to provide the user with visual-instructions in regards to a required response and/or visual-feedback in regards to the received response.

According to some embodiments, the display device is at least one selected from the group consisting of: a handheld video game device, a computer screen, a television screen, a smart phone, a tablet computer, a projector, a hologram projector, and any device that can display images to a user.

According to some embodiments, the device further comprises an audio-device such as a speaker, configured to provide the user with audio-instructions in regards to a required response and/or audio-feedback in regards to the collected response.

According to some embodiments, the dynamic images are prepared and stored by a remote server and sent to display-device via a network.

According to some embodiments, the user's response and/or analysis is stored in a database in a remote server via a network.

According to an embodiment, disclosed herein a transitory or non-transitory computer readable medium (CRM) comprising executable code instructions, which instructions when executed by a data processor cause the data processor to perform a method for presenting dynamic-images to a user, the method comprising steps of:
  displaying, at a given time-step (n=k), one or more dynamic-images to a user, via a display-device;
  receiving, at the given time-step (n=k), the user's response to the displayed dynamic-image/s, via an input-interface, where the lack of a response is also considered as a response;
  analyzing, one or more of the user's responses (n≤k), received at the given time-step (n=k) and/or at former time-step/s (n<k), to determine a change in the user's visual acuity, where the lack of a change is also considered and analyzed; and
  adjusting, for at least one of the following time-steps (n>k), one or more parameters of at least one of the dynamic-images, responsively to a predetermined threshold for the change or a predetermined state of the change.

According to some embodiments, the dynamic-images comprise at least one dynamic target-element, and at least one of:
  a background-element such as but not limited to a mask; and
  at least one dynamic distractor-element;
and wherein the one or more parameters is related to at least one of: the target-element, the background-element, and the distractor-element.

According to some embodiments, the analyzing comprises:
  classifying the response as being correct vs. incorrect; or classifying the response for its' level of correctness.

According to some embodiments, the analyzing takes into account the former adjustment/s.

According to some embodiments, the adjusting, of one or more parameters, is configured for optimizing the at least one of the dynamic-images for improving the user's visual acuity.

According to some embodiments, at least one of the parameters is related to duration of presentation. According to some embodiments, the duration of presentation is set according to a time that the at least one of the dynamic-images appears within a visual field of the user.

According to some embodiments, the at least one parameter is related to a direction of motion. According to some embodiments, the direction is collinear.

According to some embodiments, the at least one parameter is related to a velocity of motion.

According to some embodiments, the at least one parameter is related to orientation.

According to some embodiments, the at least one parameter is related to contrast.

According to some embodiments, the at least one parameter is related to spatial frequency.

According to some embodiments, the at least one parameter is related to size and/or dimension.

According to some embodiments, the at least one parameter is related to crowding, density, or distance between at least two of: dynamic target-elements, and/or dynamic distractor-elements.

According to some embodiments, the at least one parameter is related to features of the background.

According to some embodiments, the displaying of at least two of the dynamic-images is consecutive.

According to some embodiments, the at least one parameter is related to time interval between the at least two consecutive dynamic-images.

According to some embodiments, the analyzing comprises determining the user's visual acuity level, responsively to at least one threshold for number of correct or incorrect user-responses.

According to some embodiments, the adjusting further comprises replacing at least one of the dynamic-images with a new dynamic-image having same or higher level of response-challenge as of the replaced dynamic-image, responsively to an improvement in the user's visual acuity and at least one of:
  a predetermined threshold for the user's visual acuity;
  a predetermined threshold for the change.

According to some embodiments, the adjusting further comprises replacing at least one of the dynamic-images with a new dynamic-image having same or lower level of response-challenge as of the replaced dynamic-image, responsively to a decrease in the user's visual acuity and at least one of:
  a predetermined threshold for the user's visual acuity;
  a predetermined threshold for the change.

According to some embodiments, the analysing comprises detecting a vision deficiency of the user, by comparing or associating at least one of the user's responses (n≤k) with a predetermined dataset; and displaying the detection. According to some embodiments, the vision deficiency is selected from a group consisting of: amblyopia, retinopathy, and glaucoma.

According to some embodiments, the analysing comprises detecting a disability of the user, by comparing or associating at least one of the user's responses (n≤k) with a predetermined dataset; and displaying the detection. According to some embodiments, the disability is selected from a group consisting of: attention deficit disorder; attention hyperactivity disorder and dyslexia.

According to some embodiments, the detecting of the vision deficiency and/or the disability, comprises:
  the displaying, at the given time step (n=k), is a sequence of dynamic-images;
  changing one or more viewing-parameters between dynamic-images of the sequence, as the displaying of the sequence progresses, wherein the one or more viewing-parameters are selected from: spatial- and temporal-parameters; and
  calculating a vision evaluation score, according the received user's response, received at the given time-step (n=k).

According to some embodiments, the one or more viewing-parameters are selected from: physical size of one or more objects in the dynamic-images, duration of presentation of each of the dynamic-images of the sequence, contrast of each of the dynamic-images of the sequence, color of the one or more objects, color of a background of each of the dynamic-images of the sequence, number of objects in each of the dynamic-image of the sequence, and display resolution of each of the dynamic-image of the sequence.

According to some embodiments, the method further comprises providing to the user visual and/or audio instructions in regards to a required response.

According to some embodiments, the method further comprises providing to the user visual and/or audio feedback in regards to the received response.

According to some embodiments, the receiving comprises at least one of:
- collecting the user's response via a tactile and/or touch input device;
- recognizing voice of the user;
- monitoring and observing the user for at least one of: gesture, eye-motion, and brain waves.

According to some embodiments, the steps of analysing and adjusting are performed every predetermined number N of time-steps, and/or every predetermined time period.

According to some embodiments, the displaying and receiving are implemented as a game to encourage participation of the user.

According to some embodiments, the displaying is configured to one of the user's eyes or for both.

Reference is now made to FIG. 1 which is a flowchart of a method for presenting dynamic computer images to evaluate and/or improve user visual acuity, according to an embodiment of the present invention. According to some embodiments the dynamic commuter images are implemented or may be construed as a game. In a step 101 one or more target images 121 are displayed to the user on the screen of a user device 131. According to various embodiments, the user's device 131 comprises at least one of (not shown): the at least one processor 131A, the display device 131B, the input interface device 131C, and the audio device 131D, which are not shown. In various embodiments, one or more distractor images 123 are also displayed to the user on the screen of user device 131. In one related embodiment, target images 121 and distractor images 123 are prepared and stored locally on user device 131. Non-limiting examples of user devices include smartphones, tablet computers, and personal computers. In another related embodiment, target images 121 and distractor images 123 are prepared and stored by a remote server 133 and sent to user device 131 via a network 135. In still another embodiment, target images 121 and distractor images 123 are prepared and stored in a distributed fashion among devices such as user device 131 and remote server 133. Target images 121 are the images that the user is to visually acquire and identify, and, in some embodiments, to discriminate from distractor images 123. Some embodiments of the invention do not utilize distractor images, so for such embodiments, references herein to distractor images are not relevant.

In various embodiments of the invention, target images 121 and distractor images 123 are data objects which include graphical data descriptors of the respective images for display purposes, along with parameters, non-limiting examples of which include: size, shape, orientation, speed of motion, direction of motion, contrast levels and gradations, spatial frequency, color scheme, and so forth. It is also noted that the vector velocity of an object specifies both speed and direction of motion. The visual properties of the images displayed on the screen of user device 131 are determined by target image data objects 121 and distractor image data objects 123. In various embodiments of the present invention, therefore, the visual properties of the displayed images may be analyzed by analyzing target image data objects 121 and distractor image data objects 123.

In a step 103 user device 131 receives user input response related to the displayed image or images, via one or more user input devices of user device 121. According to various embodiments of the invention, there are correct responses and incorrect responses. In one embodiment, no user response after a certain period of time by the user after display of a target 121 is considered an incorrect response; in another embodiment, an input by the user in response to a distractor 123 rather than a target 121 is considered an incorrect response.

In a step 105 the user's response is recorded in a user response database 125 for analysis. According to a related embodiment, user response database 125 is stored in user device 131. In another related embodiment, user response database 125 is stored in remote server 133. In still another related embodiment, user response database 125 is stored in a distributed fashion among devices such as user device 131 and remote server 133. In some embodiments, the user's response can be a set of responses, a non-limiting example of which is a joystick movement followed by a button push.

In a step 107 the user's response is analyzed and processed. In some embodiments, step 107 is performed after recording step 105, as shown in FIG. 1. In other embodiments, step 107 is performed before recording step 105. In various embodiments of the invention, the user's response is analyzed to determine whether the user's response is a correct response or an incorrect response. In certain embodiments, the response is analyzed to determine whether there are changes to the user's visual acuity, and if so, whether the changes represent an improvement. In these embodiments, parameters of the displayed visual objects are changed according to changes in the user's visual acuity. In other embodiments of the invention, visual object display parameters are changed within a session without substantial or measureable change in visual acuity. In a related embodiment, parameters are changed with the goal of revealing a future change in visual acuity In a related embodiment, the analysis and processing of the user's response is done by user device 131. In another related embodiment, the analysis and processing of the user's response is done by remote server 133. In still another related embodiment, the analysis and processing of the user's response is done in a distributed fashion among devices such as user device 131 and remote server 133.

In some embodiments, a step 109 provides feedback to the user related to the user's response. In related embodiments, there is feedback for a correct response and different feedback for an incorrect response. In other embodiments, feedback is not provided. In still other embodiments, feedback varies according to response, and may include sounds, images, and text.

Various embodiments of the invention provide sets of adaptive methods for analysis and processing of the user's responses to targets 121 and distractors 123 that have been displayed, and how the responses relate to the visual properties of the targets 121 and distractors 123.

According to an embodiment of the invention, a step 109 provides feedback to the user via user device 131. According to various embodiments, a step 111 provides adjustment for the parameters of target images 121 and distractor images 123, wherein the adjustment optimizes the capability to improve the player's visual acuity. Related embodiments are discussed below, with reference to FIG. 2A and FIG. 2B.

Figure 2A:
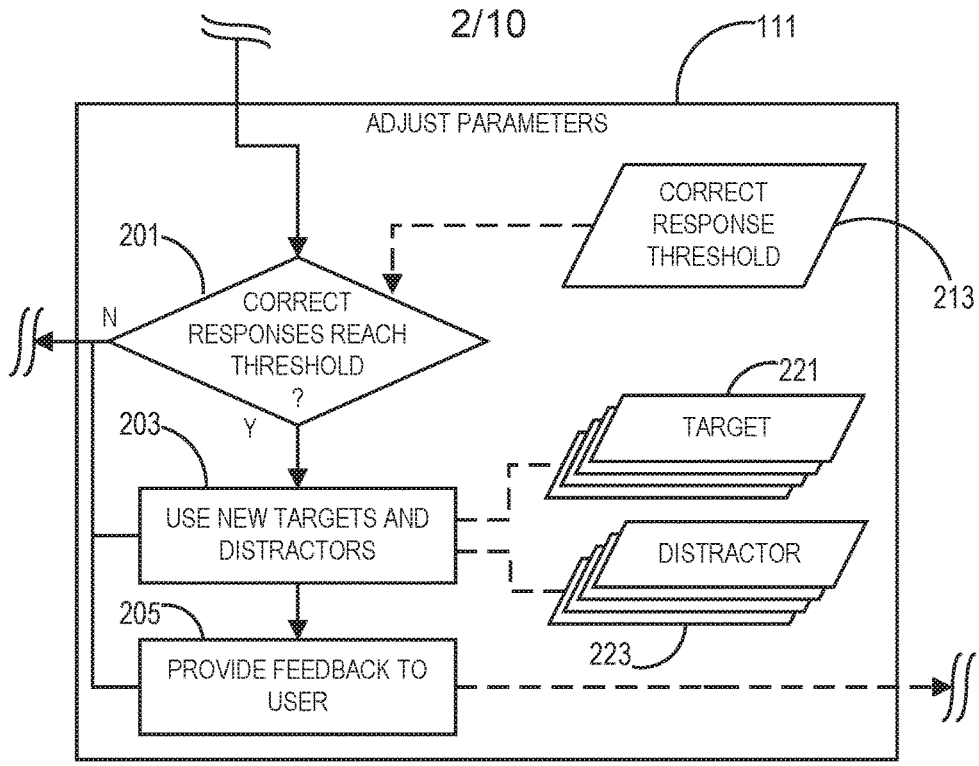
FIG. 2A is a flowchart of a method for adaptive adjustment of image parameters, according to an embodiment of the present invention.

FIG. 2A is a flowchart of a method for adaptive adjustment of image parameters in step 111, according to one of the related embodiments mentioned above. At a decision point 201 it is determined whether or not the user's visual acuity is above a given level. In a related embodiment, determining whether or not the user's visual acuity is above a given level is done by determining whether or not the number of correct user responses has reached a threshold 213. If the number of correct user responses has not reached threshold 213, then the method continues with a return to step 101 as shown in FIG. 1. If, however, the number of correct user responses has reached threshold 213, then the method continues with a step 203, in which new target images 221 and new distractor images 223 replace target images 121 and distractor images 123 (FIG. 1). In a related embodiment, the visual properties of new target images 221 and new distractor images 223 present the user with the same level of challenge as target images 121 and distractor images 123. In another related embodiment, the visual properties of new target images 221 and new distractor images 223 present the user with a higher level of challenge than target images 121 and distractor images 123.

Figure 2B:
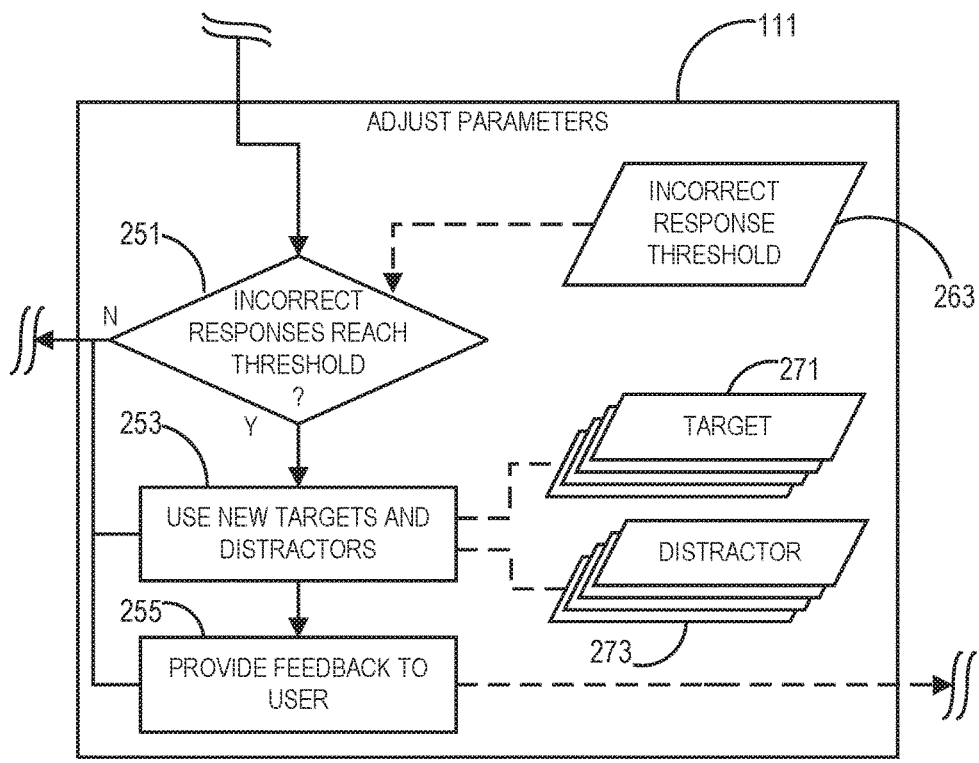
FIG. 2B is a flowchart of a method for adaptive adjustment of image parameters, according to another embodiment of the present invention.

FIG. 2B is a flowchart of a method for adaptive adjustment of image parameters in step 111, according to the other of the related embodiments mentioned above. At a decision point 251 it is determined whether or not the user's visual acuity is below a given level. In a related embodiment, determining whether or not the user's visual acuity is below a given level is done by determining whether or not the number of incorrect user responses has reached a threshold 263. If the number of incorrect user responses has not reached threshold 263, then the method continues with a return to step 101 as shown in FIG. 1. If, however, the number of incorrect user responses has reached threshold 263, then the method continues with a step 253, in which new target images 271 and new distractor images 273 replace target images 121 and distractor images 123 (FIG. 1). In a related embodiment, the visual properties of new target images 271 and new distractor images 273 present the user with the same level of challenge as target images 121 and distractor images 123. In another related embodiment, the visual properties of new target images 271 and new distractor images 273 present the user with a lower level of challenge than target images 121 and distractor images 123.

Figure 3:
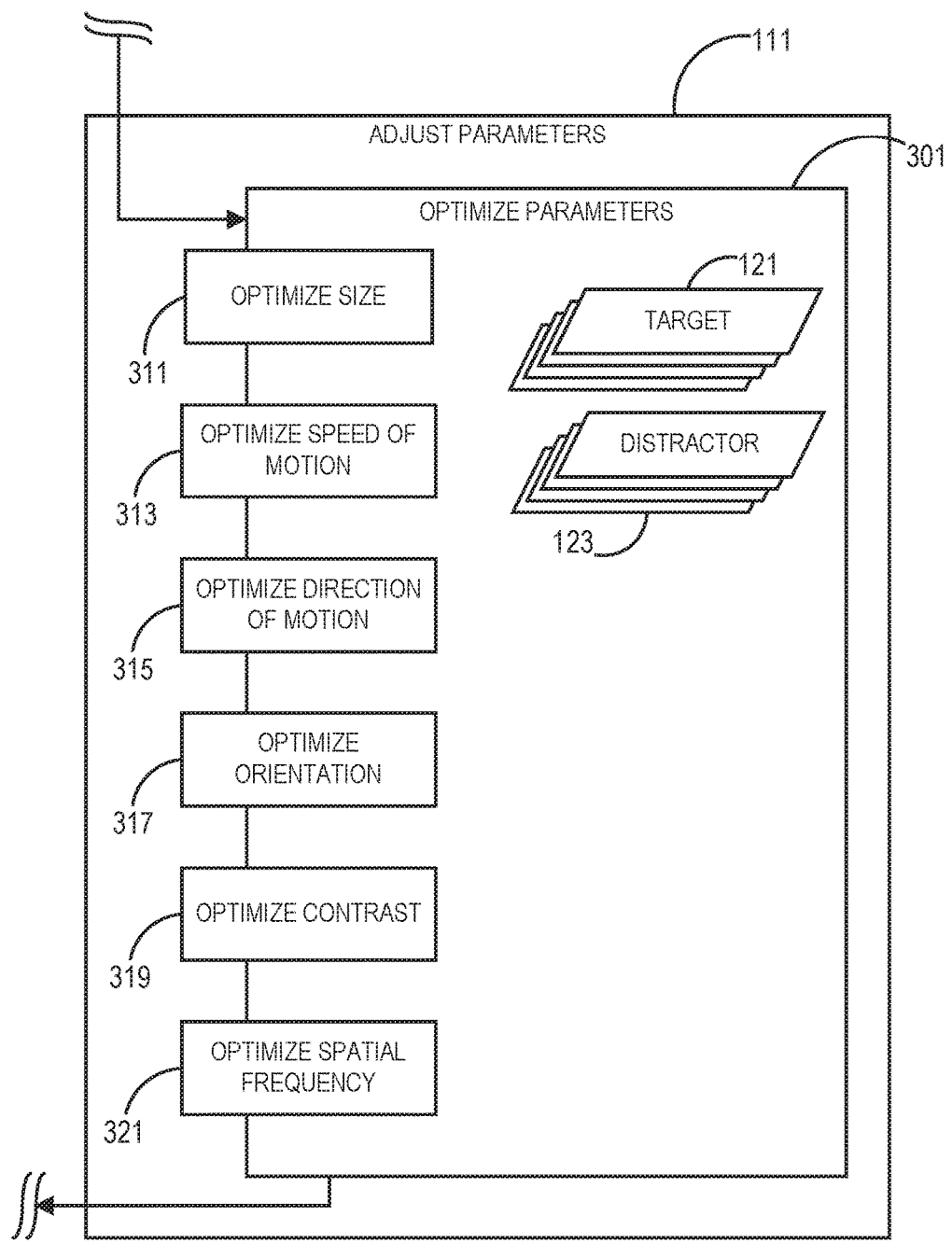
FIG. 3 is a flowchart of a method for adaptive optimization of image parameters, according to certain embodiments of the present invention.

FIG. 3 is a flowchart of a method for adaptive optimization of image parameters, according to certain embodiments of the present invention. In these embodiments, optimization is to adjust the image parameters to effect an improvement in the visual acuity of the user. A step 301 optimizes parameters of target images 121 and distractor images 123. As previously noted, some embodiments of the invention do not utilize distractor images, so for such embodiments, references herein to distractor images are not relevant.

In an embodiment of the invention, image size is optimized in a step 311. In another embodiment, image motion speed is optimized in a step 313. In another embodiment, image motion direction is optimized in a step 315. In another embodiment, image orientation is optimized in a step 317. In another embodiment, image contrast is optimized in a step 319. In another embodiment, spatial frequency of the image is optimized in a step 321. In these various embodiments, the parameters of the images are adjusted according to known neural behavior characteristics, non-limiting examples of which include: application of [Equations 1], [Equation 2], or [Equation 3] above, regarding image motion speed; and adjusting the direction of image motion according to a collinear direction.

According to further embodiments of the present invention, there is provided a computer game-playing device application which includes executable code stored in non-transitory media for use with a computer game-playing device, such that when the executable computer code is run on the device, the device performs a method of the present invention as disclosed herein, including the methods illustrated in FIG. 1, FIG. 2A, FIG. 2B, FIG. 3 and FIG. 4. In a related embodiment, the computer game-playing device is a user device.

Figure 4:
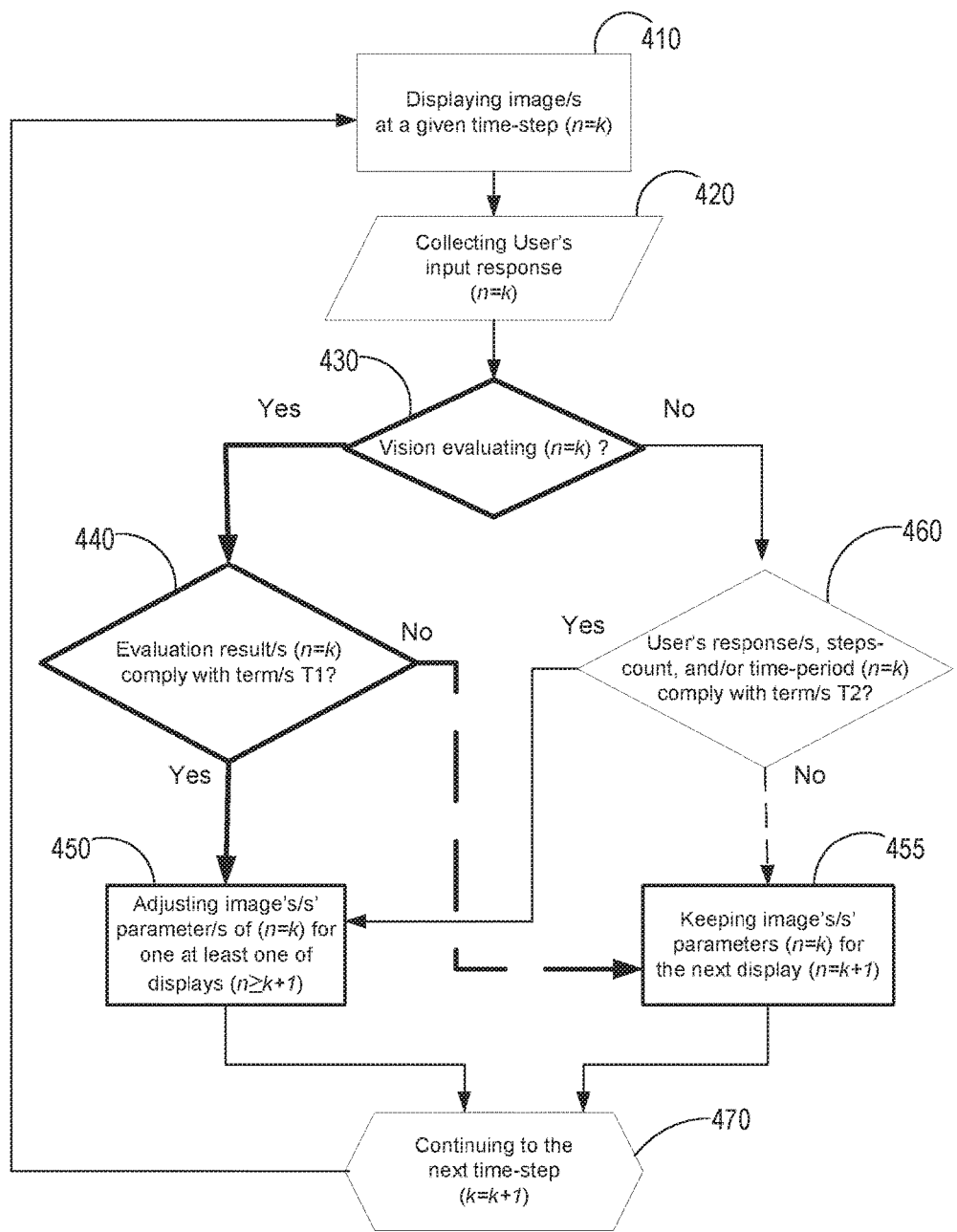
FIG. 4 is a flowchart demonstrating optional operation for the disclosed methods.

FIG. 4 is a flowchart demonstrating optional operations for the disclosed methods, according to various embodiments of the invention. Step 410 demonstrates the displaying of at least one dynamic image to the user, at a given time-step (n=k). Step 420 demonstrates the collecting of the user's response to the displayed dynamic image/s, at the given time-step (n=k).

According to some embodiments, the steps of analysing and adjusting are performed every predetermined number N of time-steps, and/or every predetermined time period. Accordingly step 430 allows two options, for the current given time-step (n=k):

analysing the user's response in terms of vision evaluating (Yes), thereby continue to step 440; or, analysing the user's response for its mere level of correctness (No), thereby continue to step 460.

According to some embodiments, in the case of analysing the user's response in terms of vision evaluating (Yes), step 450 shows the analyzing one or more of the user's responses (n≤k), received at the given time-step (n=k) and/or at former time-step/s (n<k), to determine a change in the user's visual acuity; and if the determined change complies or achieves a predetermined threshold or a predetermined state for the change (term/s T1), the method continues to (Yes) step 450, otherwise to (No) step 455.

According to some embodiments, in the case of not analysing the user's response in terms of vision evaluating (No), step 460 shows the analyzing one or more of the user's responses (n≤k), received at the given time-step (n=k) and/or at former time-step/s (n<k) for its mere correctness; and if at least one of: the user's response/s at (n≤k), number of time-steps at (n≤k), and time-period at (n≤k), comply with a predetermined threshold or a predetermined state (term/s T2), the method continues to (Yes) step 450, otherwise to (No) step 455.

According to some embodiments, step 450 shows the adjusting of the image's/s' parameter/s of the given time-step (n=k), for at least one of the following displays (n≥k+1), according to the analysing of step 440 or step 460 results.

According to some embodiments, step 455 shows the keeping of the image's/s' parameter/s of the given time-step (n=k) for at least the next displaying of the next time-step (n=k+1).

According to some embodiments, step 470 demonstrates the actual shifting to the next time-step, thereby k=k+1.

EXAMPLES

FIGS. 5-10 present the tests and the results for an investigation conducted for demonstrating the enhancement of visual functions, for 20 participants ages 20-40 with normal vision, using the above mentioned game-like dynamic training.

The training included dynamic game-like tasks, presented on mobile iOS devices (with retina resolution), from a distance of about 40 cm.

The tasks, given to the participants, were to detect low contrast of moving targets (Gabor patches) embedded between high contrast collinear moving flankers, with or without temporal backward masking (BM) and/or lateral masking (LM).

The participants were tested before and after the above mentioned training. The testing was conducted in a laboratory, on PC screen, from a distance of about 1.5 meters.

Figure 5A:
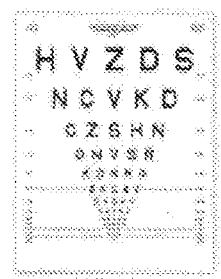
FIGS. 5A-5C demonstrate certain embodiments of the present invention, presenting for example the static visual acuity test and its results.
Figure 6A:
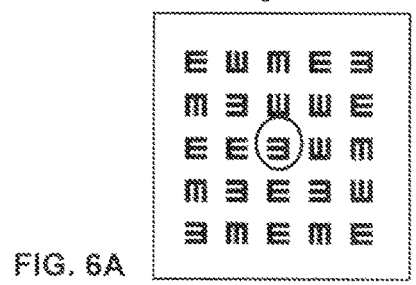
FIGS. 6A-6C demonstrate certain embodiments of the present invention, presenting for example the crowding effect test and its results.
Figure 7A:
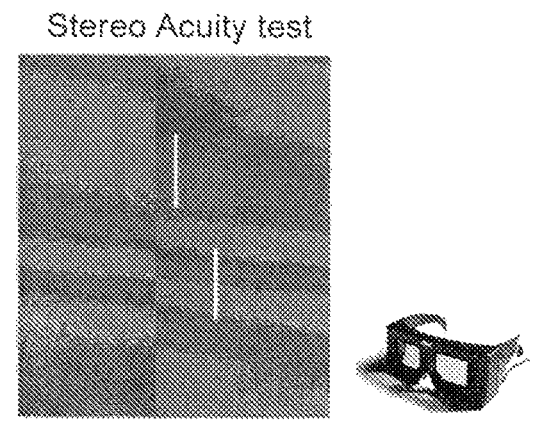
FIGS. 7A-7B demonstrate certain embodiments of the present invention, presenting for example the stereo acuity test and its results.
Figure 8A:
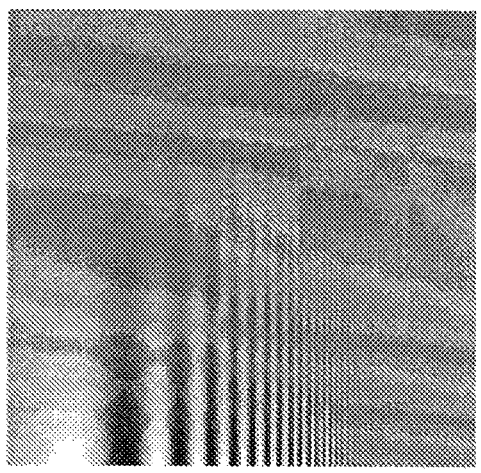
FIGS. 8A-8B demonstrate certain embodiments of the present invention, presenting for example the contrast sensitivity test and its results.
Figure 9A:
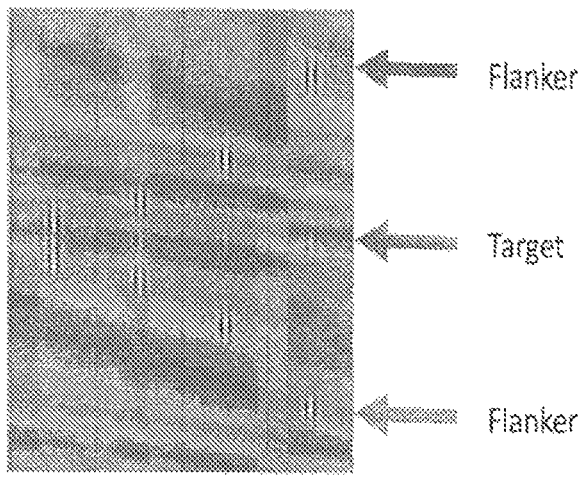
FIGS. 9A-9B demonstrate certain embodiments of the present invention, presenting for example the complex contrast sensitivity test and its results.
Figure 10A:
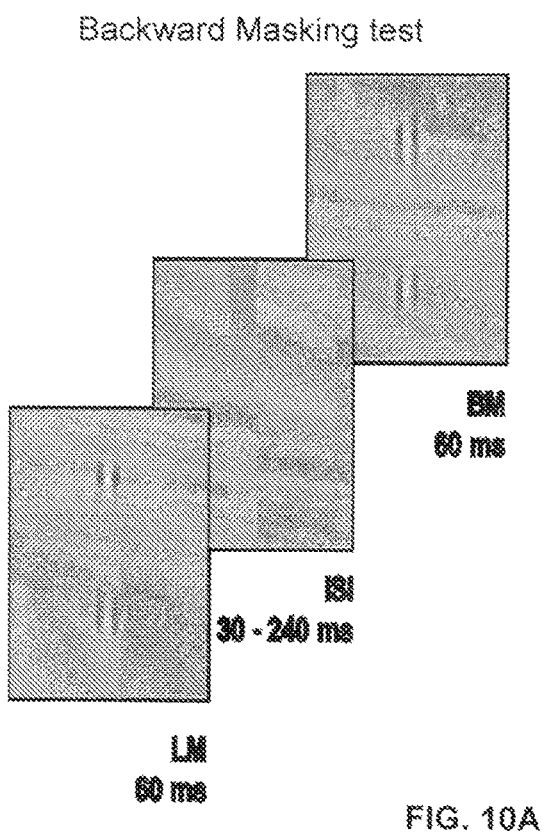
FIGS. 10A-10B demonstrate certain embodiments of the present invention, presenting for example backward/lateral masking test and its results.

The following were images tested and measured:
near/far static visual acuity, as shown in FIG. 5A, testing: left eye (LE), right eye (RE), and both eyes (BE) together, tested from a variety of distances, for example about 40 cm for the near visual acuity and about 1.5 m, 3 m or even more for the far visual acuity;
foveal crowding, as shown in FIG. 6A, testing the reaction time for different image presentation time;
stereo acuity, as shown in FIG. 7A, testing the response for different image presentation time;
contrast detection, as shown in FIG. 8A, testing the response for different image presentation time;
complex contrast detection with flakers, as shown in FIG. 9A, testing the response for different spatial resolutions; and
backward masking, as shown in FIG. 10A, testing the response for different inter stimulus interval (ISI).

The overall time for the training sessions was about 3.5 hours, including: two non-sequential training of 4-5 minutes sessions per day; 3-4 times per week, for a total of 40 sessions.

FIGS. 5-10 demonstrate that the dynamic training achieved remarkable improvements in visual performance, even more than the results achieved with static training, in some visual parameters such as distance visual acuity, as measured with the clinical chart (compared to the results published by Lev et al. *Scientific Reports* 2014)

Figure 5B:
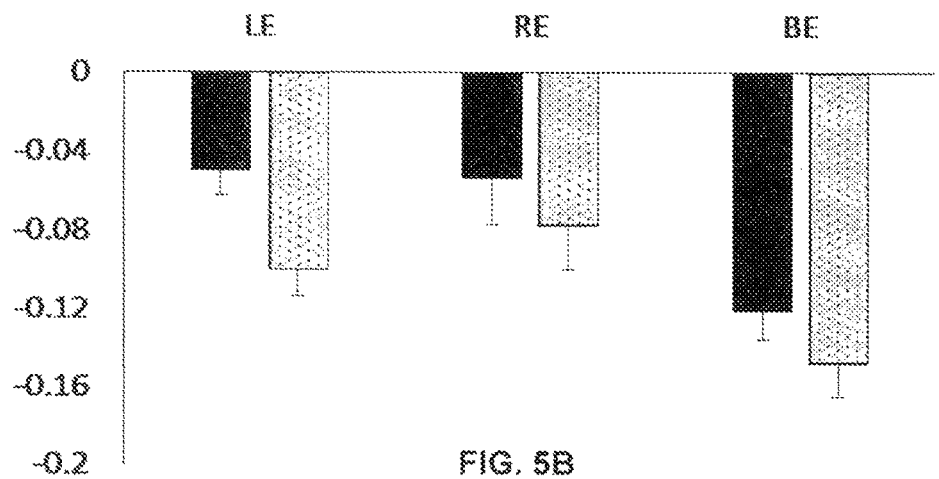
Figure 5C:
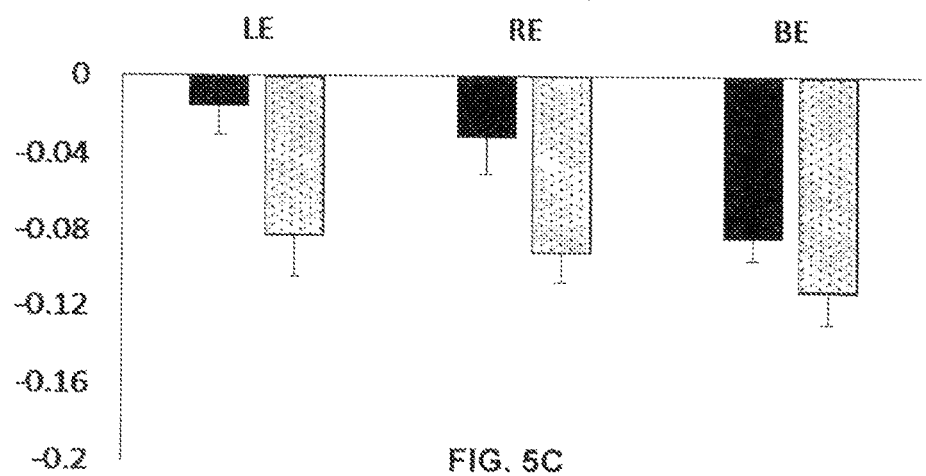

FIG. 5A demonstrates the static visual acuity test, for example the ETDRS Chart, and its results are presented in FIGS. 5B and 5C. The results are shown for: left eye (LE), right eye (RE), and for both eyes (BE) tested together, for distant visual acuity as in FIG. 5B and for near visual acuity as in FIG. 5C. The results before the training are denoted on the left (plain) columns and the results after the training are denoted on the right (doted) columns.

Figure 6B:
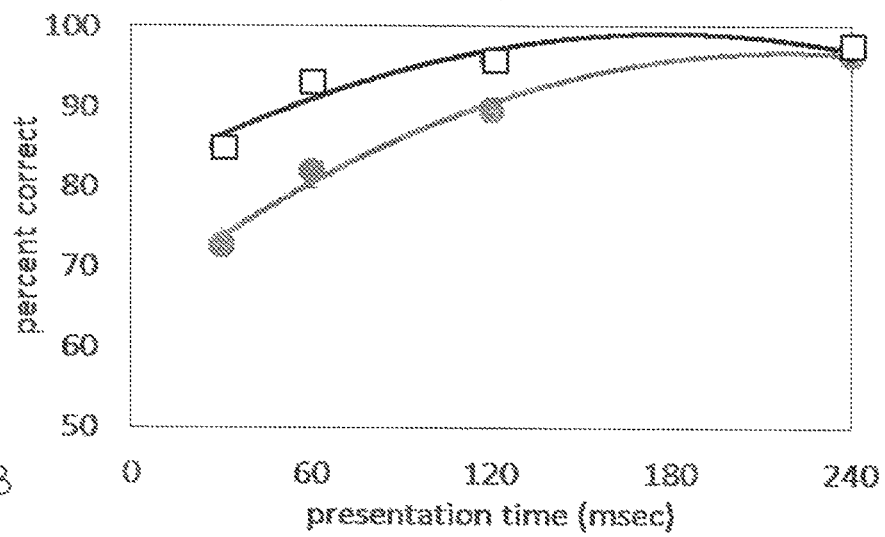
Figure 6C:
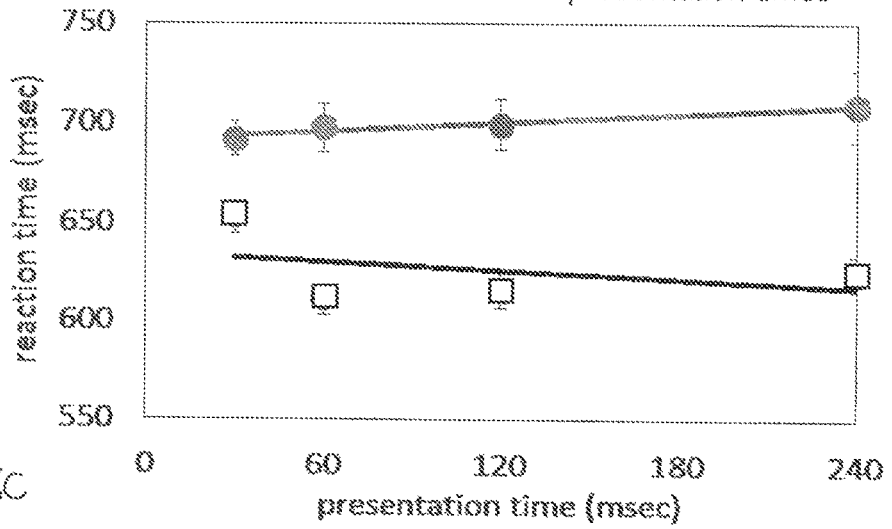

FIG. 6A demonstrates the crowding effect test and its results are presented in FIGS. 6B and 6C. The results are shown for different image presentation times, as in FIG. 6B, and the reaction time for the different image presentation times, as shown in FIG. 6C. The results before the training are denoted in circles and the results after the training are denoted in squares.

Figure 7B:
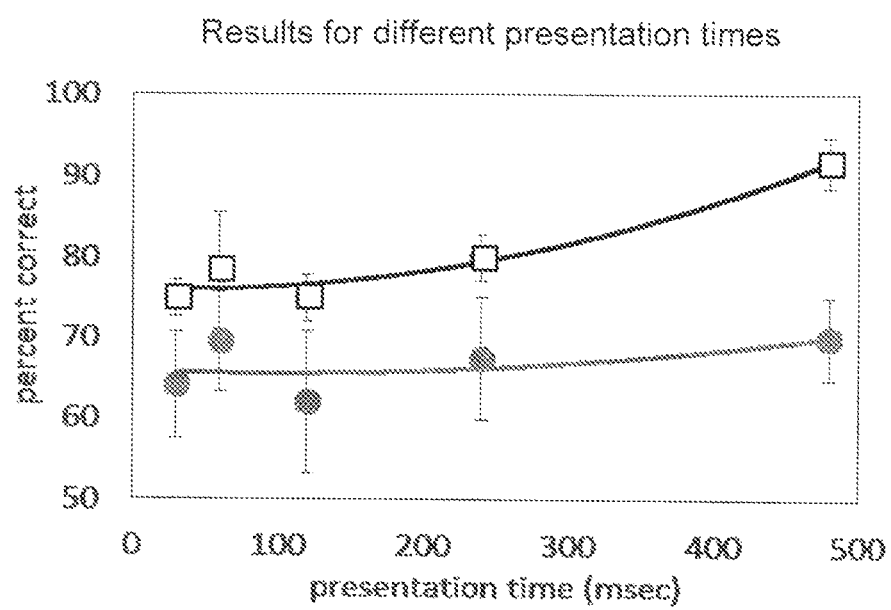

FIG. 7A demonstrates the stereo acuity test and its results for different image presentation times are presented in FIG. 7B. The results before the training are denoted in circles and the results after the training are denoted in squares.

Figure 8B:
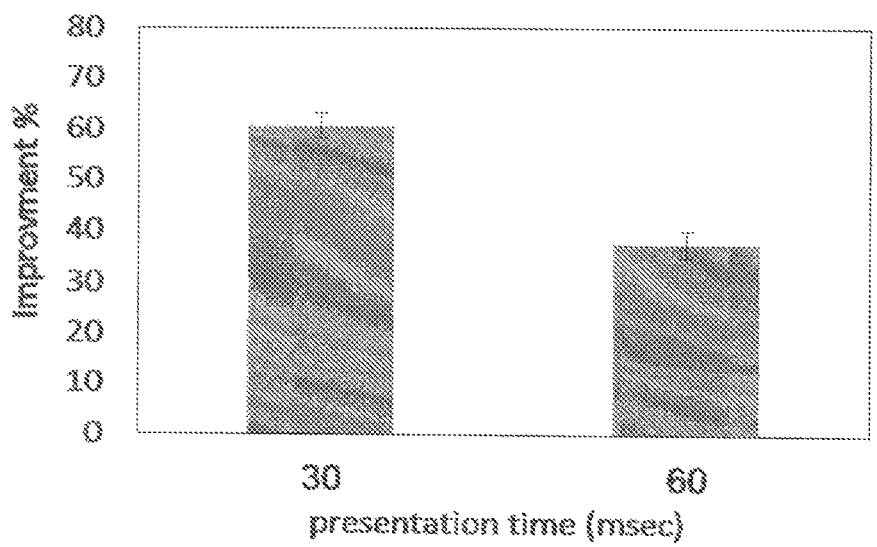

FIG. 8A demonstrates the contrast sensitivity test and its results for different image presentation times are presented in FIG. 8B.

Figure 9B:
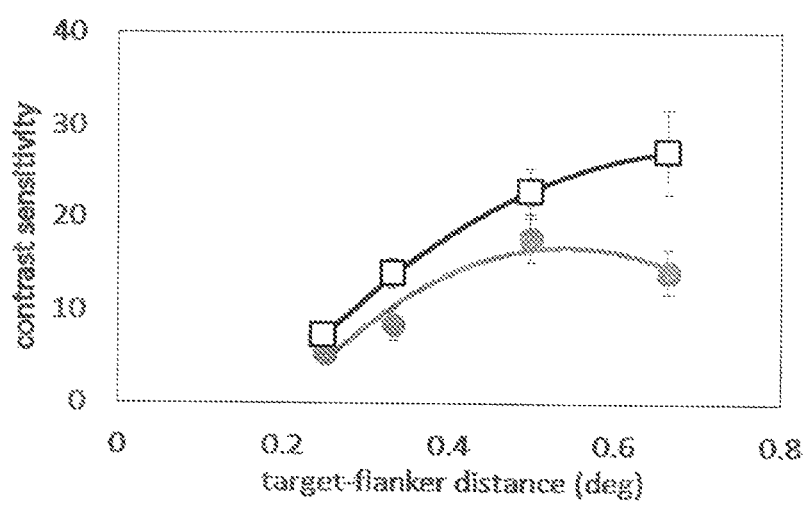

FIG. 9A demonstrates the complex contrast sensitivity test with target flankers and its results for different target-flankers distances are presented in FIG. 9B. The results before the training are denoted in circles and the results after the training are denoted in squares.

Figure 10B:
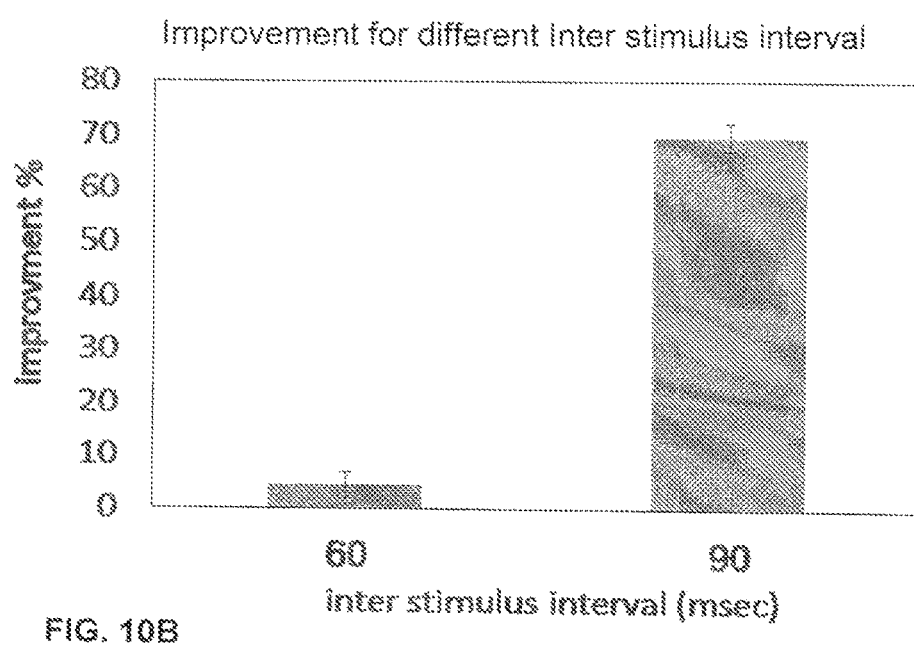

FIG. 10A demonstrates backward masking (BM) and lateral masking (LM) test and its results for different Inter stimulus intervals (ISI) are presented in FIG. 10B.

CONCLUSIONS

The results, as demonstrated in FIGS. 5-10, demonstrate a significant improvement after following the training in far/near visual acuity, stereo acuity, contrast sensitivity, reduction of crowding effect and decrease of reaction time.

The improvement of contrast sensitivity, crowding and stereo acuity together with improvement in temporal masking and reaction time suggest an increase of visual processing speed.

The results suggest that it is possible to enhance visual functions to more superior level with dynamic game-like tasks using very short training sessions.

The training may contribute to enhance visual skills of athletes whose performance relies on visual abilities.

It is understood that various other modifications will be readily apparent to those skilled in the art without departing from the scope and spirit of the invention. Accordingly, it is not intended that the scope of the claims appended hereto be limited to the description set forth herein, but rather that the claims be construed as encompassing all the features of the patentable novelty that reside in the present invention, including all features that would be treated as equivalents thereof by those skilled in the art to which this invention pertains.

What is claimed is:

1. A method for presenting dynamic-images to a user, the method comprising processor implemented steps of:
    displaying, at a given time-step (n=k), one or more dynamic-images to the user, wherein a dynamic-image is an image initially displayed at a specific location and moving to another location, during the given time-step (n=k);
    receiving, at the given time-step (n=k), the user's response to the displayed dynamic-image/s;
    analyzing, one or more of the user's responses, received at the given time-step (n=k) and/or at former time-step/s (n<k), to determine a change in the user's visual acuity; and
    adjusting, for at least one of the following time-steps (n>k), one or more parameters of at least one of the dynamic-images, responsively to a predetermined threshold for—or a state of—the change.

2. The method of claim 1, wherein the dynamic-images comprise at least one dynamic target-element and at least one of:
    a background-element and
    at least one dynamic distractor-element;
    and wherein the one or more parameters is related to at least one of: the target-element, the background-element, and the distractor-element.

3. The method of claim 1, wherein at least one of the following holds true:
    the analyzing comprises classifying the response as being correct vs. incorrect, or classifying the response for its' level of correctness;
    the analyzing takes into account former adjustment/s;
    the at least one parameter is related to at least one of: direction of motion, velocity of motion; orientation of motion, contrast, spatial frequency, size and/or dimension;
    the method further comprising providing to the user visual and/or audio instructions in regards to a required response;
    the method further comprising providing to the user visual and/or audio feedback in regards to the received response;
    the steps of analysing and adjusting are performed every predetermined number N of time-steps, and/or every predetermined time period;
    the displaying and receiving are implemented as a game to encourage participation of the user; and the displaying is configured for one of the user's eyes or for both.

4. The method of claim 1, wherein at least one of the parameters is related to duration of presentation.

5. The method of claim 4, wherein the duration of presentation is set according to a time that the at least one of the dynamic-images appears within a neuron's visual field of the user.

6. The method of claim 2, wherein the at least one parameter is related to crowding, density, or distance between at least two of: dynamic target-elements, and/or dynamic distractor-elements.

7. The method of claim 2, wherein the at least one parameter is related to features of the background.

8. The method of claim 1, wherein the displaying of at least two of the dynamic-images is consecutive.

9. The method of claim 8, wherein the at least one parameter is related to time interval between the at least two consecutive dynamic-images.

10. The method of claim 1, wherein the analyzing comprises determining the user's visual acuity level, responsively to at least one threshold for number of correct or incorrect user-responses.

11. The method of claim 1, wherein the adjusting further comprises replacing at least one of the dynamic-images with a new dynamic-image having same or higher level of response-challenge as of the replaced dynamic-image, responsively to an improvement in the user's visual acuity and at least one of:
   a predetermined threshold for the user's visual acuity;
   a predetermined threshold for the change.

12. The method of claim 1, wherein the adjusting further comprises replacing at least one of the dynamic-images with a new dynamic-image having same or lower level of response-challenge as of the replaced dynamic-image, responsively to a decrease in the user's visual acuity and at least one of:
   a predetermined threshold for the user's visual acuity;
   a predetermined threshold for the change.

13. The method of claim 1, the analyzing further comprises detecting a vision deficiency of the user, by comparing or associating at least one of the user's responses (n≤k) with a predetermined dataset; and displaying the detection.

14. The method of claim 13, wherein the vision deficiency is selected from a group consisting of: amblyopia, retinopathy, and glaucoma.

15. The method of claim 1, the analyzing further comprises detecting a disability of the user, by comparing or associating at least one of the user's responses (n≤k) with a predetermined dataset; and displaying the detection.

16. The method of claim 1, wherein the receiving comprises at least one of:
   collecting the user's response via a tactile and/or touch input device;
   recognizing voice of the user;
   monitoring and observing the user for at least one of: gesture, eye-motion, and brain waves.

17. A device configured to display dynamic images to a user, comprising:
   at least one display-device, configure to display, at a given time-step (n=k), one or more dynamic-images to the user, wherein a dynamic-image is an image initially displayed at a specific location and moving to another location, during the given time-step (n=k);
   at least one input-device, configured to collect and interpret, at the given time-step (n=k), the user's response to the displayed dynamic-image/s; and
   at least one processor configured to:
      analyze, one or more of the user's responses, received at the given time-step (n=k) and/or at former time-step/s (n <k), to determine a change in the user's visual acuity; and
      adjust, for at least one of the following time-steps (n>k), one or more parameters of at least one of the dynamic-images, responsively to a predetermined threshold for—or a state of—the change.

18. The device of claim 17, wherein the input-device is configured to perform at least one of:
   collect tactile—and/or touch—input of the user;
   recognize voice response of the user;
   monitor and observe the user for at least one of: gesture, eye-motion, and brain waves.

19. The device of claim 17, wherein at least one of the following holds true:
   the display-device, is configured to provide the user with visual-instructions in regards to a required response and/or visual-feedback in regards to the received response;
   the device further comprising an audio-device, configured to provide the user with audio-instructions in regards to a required response and/or audio-feedback in regards to the collected response;
   the dynamic images are prepared and stored by a remote server and sent to display-device via a network;
   the user's response and/or analysis is stored in a database in a remote server via a network; and
   the display-device is configured for displaying for one of the user's eyes or for both.

20. A non-transitory computer readable medium (CRM) comprising executable code instructions, which instructions when executed by a data processor cause the data processor to perform a method for presenting dynamic-images to a user, the method comprising steps of:
   displaying, at a given time-step (n=k), one or more dynamic-images to the user, wherein a dynamic-image is an image initially displayed at a specific location and moving to another location, during the given time-step (n=k);
   receiving, at the given time-step (n=k), the user's response to the displayed dynamic-image/s;
   analyzing, one or more of the user's responses, received at the given time-step (n=k) and/or at former time-step/s (n<k), to determine a change in the user's visual acuity; and
   adjusting, for at least one of the following time-steps (n>k), one or more parameters of at least one of the dynamic-images, responsively to a predetermined threshold for—or a state of—the change.

* * * * *